US010653508B2

(12) United States Patent
Bailly et al.

(10) Patent No.: US 10,653,508 B2
(45) Date of Patent: *May 19, 2020

(54) TEXTILE-BASED PROSTHESIS FOR TREATMENT OF INGUINAL HERNIA

(71) Applicant: Sofradim Production, Trévoux (FR)

(72) Inventors: Pierre Bailly, Caluire-et-Cuire (FR); Mylene Desorme, Villeurbanne (FR); Genevieve Doucet, Villefrancehe sur Saone (FR)

(73) Assignee: Sofradim Production, Trévoux (FR)

( * ) Notice: Subject to any disclaimer, the term of this patent is extended or adjusted under 35 U.S.C. 154(b) by 217 days.

This patent is subject to a terminal disclaimer.

(21) Appl. No.: 15/838,528

(22) Filed: Dec. 12, 2017

(65) Prior Publication Data

US 2018/0098835 A1    Apr. 12, 2018

Related U.S. Application Data

(63) Continuation of application No. 14/860,743, filed on Sep. 22, 2015, now Pat. No. 9,877,820.

(30) Foreign Application Priority Data

Sep. 29, 2014  (EP) .................................. 14306520

(51) Int. Cl.
*A61F 2/00* (2006.01)
(52) U.S. Cl.
CPC .... *A61F 2/0063* (2013.01); *A61F 2002/0072* (2013.01); *A61F 2210/0004* (2013.01);
(Continued)
(58) Field of Classification Search
CPC ............ A61F 2/0063; A61F 2002/0072; A61F 2210/0004; A61F 2220/005;
(Continued)

(56) References Cited

U.S. PATENT DOCUMENTS

| 1,187,158 A | 6/1916 | Mcginley |
| 3,118,294 A | 1/1964 | Van Laethem |
| (Continued) | | |

FOREIGN PATENT DOCUMENTS

| CA | 1317836 C | 5/1993 |
| DE | 19544162 C1 | 4/1997 |
| (Continued) | | |

OTHER PUBLICATIONS

Examination report No. 1 issued in Australian Patent Application No. 2015221457 dated Jun. 3, 2019, 4 pages.

(Continued)

*Primary Examiner* — Jocelin C Tanner

(57) ABSTRACT

The invention relates to a prosthesis (1) for the repair of an inguinal hernia comprising:
  a textile (2) of elongate shape,
  a resilient frame (3) connected to said textile,
characterized in that said frame comprises a convex cranial segment (3c), a caudal segment (3d),
  a lateral corner segment (3b) joining together the convex cranial segment and the caudal segment, and a folding segment (5) joining a medial end of said convex cranial segment to a point located on the caudal segment while leaving the region of the medial end of the textile free of any frame,
  said frame being able to adopt an unstressed configuration, in which said textile is deployed, and a stressed configuration, in which said convex cranial segment, said caudal segment and said folding segment are substantially collected together and aligned on one folding direction, said textile forming thereby at least one fold along said folding direction.

22 Claims, 5 Drawing Sheets

(52) U.S. Cl.
CPC . *A61F 2220/005* (2013.01); *A61F 2220/0058* (2013.01); *A61F 2220/0075* (2013.01); *A61F 2230/0008* (2013.01); *A61F 2250/0031* (2013.01)

(58) Field of Classification Search
CPC ...... A61F 2220/0058; A61F 2220/0075; A61F 2230/0008; A61F 2250/0031
See application file for complete search history.

(56) References Cited

U.S. PATENT DOCUMENTS

| | | |
|---|---|---|
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |

(56) References Cited

U.S. PATENT DOCUMENTS

| | | |
|---|---|---|
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakamam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Muller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,743,435 B2 | 6/2004 | DeVore et al. |
| 6,755,868 B2 | 6/2004 | Rousseau |
| 6,773,723 B1 | 8/2004 | Spiro et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,670,380 B2 | 3/2010 | Cauthen, III |
| 9,877,820 B2 * | 1/2018 | Bailly .................. A61F 2/0063 |
| 2001/0008930 A1 | 7/2001 | Tayot et al. |
| 2002/0095218 A1 | 7/2002 | Carr et al. |
| 2002/0116070 A1 | 8/2002 | Amara et al. |
| 2003/0013989 A1 | 1/2003 | Obermiller et al. |
| 2003/0023316 A1 | 1/2003 | Brown et al. |
| 2003/0086975 A1 | 5/2003 | Ringeisen |
| 2003/0100954 A1 | 5/2003 | Schuldt-Hempe et al. |
| 2003/0114937 A1 | 6/2003 | Leatherbury et al. |
| 2003/0133967 A1 | 7/2003 | Ruszczak et al. |
| 2003/0212460 A1 | 11/2003 | Darois et al. |
| 2003/0225355 A1 | 12/2003 | Butler |
| 2003/0232746 A1 | 12/2003 | Lamberti et al. |
| 2004/0034373 A1 | 2/2004 | Schuldt-Hempe et al. |
| 2004/0054406 A1 | 3/2004 | Dubson et al. |
| 2004/0059356 A1 | 3/2004 | Gingras |
| 2004/0101546 A1 | 5/2004 | Gorman et al. |
| 2004/0138762 A1 | 7/2004 | Therin et al. |
| 2004/0172048 A1 | 9/2004 | Browning |
| 2004/0215219 A1 | 10/2004 | Eldridge et al. |
| 2005/0002893 A1 | 1/2005 | Goldmann |
| 2005/0010306 A1 | 1/2005 | Priewe et al. |

(56) References Cited

U.S. PATENT DOCUMENTS

| | | | |
|---|---|---|---|
| 2005/0021058 A1 | 1/2005 | Negro | |
| 2005/0085924 A1 | 4/2005 | Darois et al. | |
| 2005/0113849 A1 | 5/2005 | Popadiuk et al. | |
| 2005/0113938 A1 | 5/2005 | Jamiolkowski et al. | |
| 2005/0137512 A1 | 6/2005 | Campbell et al. | |
| 2005/0142161 A1 | 6/2005 | Freeman et al. | |
| 2005/0148963 A1 | 7/2005 | Brennan | |
| 2005/0175659 A1 | 8/2005 | Macomber et al. | |
| 2005/0228408 A1 | 10/2005 | Fricke et al. | |
| 2005/0232979 A1 | 10/2005 | Shoshan | |
| 2005/0244455 A1 | 11/2005 | Greenawalt | |
| 2005/0267521 A1 | 12/2005 | Forsberg | |
| 2005/0288691 A1 | 12/2005 | Leiboff | |
| 2006/0064175 A1 | 3/2006 | Pelissier et al. | |
| 2006/0094318 A1 | 5/2006 | Matsuda et al. | |
| 2006/0135921 A1 | 6/2006 | Wiercinski et al. | |
| 2006/0147501 A1 | 7/2006 | Hillas et al. | |
| 2006/0167561 A1 | 7/2006 | Odar et al. | |
| 2006/0216320 A1 | 9/2006 | Kitazono et al. | |
| 2006/0252981 A1 | 11/2006 | Matsuda et al. | |
| 2007/0031474 A1 | 2/2007 | Tayot | |
| 2007/0161109 A1 | 7/2007 | Archibald et al. | |
| 2007/0280990 A1 | 12/2007 | Stopek | |
| 2007/0297987 A1 | 12/2007 | Stad et al. | |
| 2007/0299538 A1 | 12/2007 | Roeber | |
| 2008/0306497 A1 | 12/2008 | Brown et al. | |
| 2013/0178875 A1 | 7/2013 | Horton et al. | |
| 2014/0379007 A1 | 12/2014 | Soares Da Costa et al. | |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1216717 A1 | 6/2002 |
| EP | 1216718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2715405 A1 | 7/1995 |
| FR | 2 724 563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2 051 153 A | 1/1981 |
| JP | H0332677 A | 2/1991 |
| JP | H05237128 A | 9/1993 |
| JP | H09137380 A | 5/1997 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 96/41588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0007520 A1 | 2/2000 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 2002/007648 | 1/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2009031035 A2 | 3/2009 |
| WO | 2009071998 A2 | 6/2009 |
| WO | 2012047414 A1 | 4/2012 |
| WO | 2013007535 A1 | 1/2013 |
| WO | 2013048272 A1 | 4/2013 |
| WO | 2014195388 A1 | 12/2014 |

OTHER PUBLICATIONS

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Enclose., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type

(56) References Cited

OTHER PUBLICATIONS

1-Infected T-Cell Lines and Primary Adult T-Cell Leukemia Cells," Nutrition and Cancer, 2005, pp. 189-201, 52(2),published online Nov. 2009.
Junge, K. et al., "Functional and Morphologic Properties of a Modified Mesh for Inguinal Hernia Repair," World J. Surg., Sep. 2002, pp. 1472-1480, 26.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004,pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern brown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Preliminary Search Report from French Patent Office dated Dec. 20, 2006, 3 pages.
European Search Report for EP 14306520.9 dated Apr. 17, 2015 (8 pages).
Communication pursuant to Article 94(3) EPC issued in corresponding European Patent Application No. 14306520.9 dated Sep. 29, 2019, 5 pages.

* cited by examiner

TEXTILE-BASED PROSTHESIS FOR TREATMENT OF INGUINAL HERNIA

CROSS-REFERENCE TO RELATED APPLICATIONS

This application is a continuation of U.S. patent application Ser. No. 14/860,743 filed Sep. 22, 2015, which claims benefit of and priority to European Patent Application Serial No. 14306520.9 filed Sep. 29, 2014, the disclosure of the above-identified application is hereby incorporated by reference in its entirety.

BACKGROUND OF THE INVENTION

The present invention relates to a prosthesis comprising a biocompatible textile and a reinforcing element of said textile, the prosthesis being intended to be used for repair of inguinal hernias.

BRIEF SUMMARY OF THE INVENTION

In this application, the "medial" end or part of an element of a prosthesis is to be understood as meaning the end or part of the element located in the direction of the median plane of the body when the prosthesis is implanted in the body. The "lateral" end or part of an element of a prosthesis is to be understood as meaning the end or part of the element located in the direction of the outwards lateral plane of the body when the prosthesis is implanted in the body. Likewise, in this application, the "medial direction" is to be understood as meaning the direction towards said median plane and the "lateral direction" is opposite the "medial direction", the medial and lateral directions being aligned on the same axis, the medial-lateral axis. In this application, the "cranial" end or part of an element of a prosthesis is to be understood as meaning the end or part of the element located substantially in the direction of the head of the body when the prosthesis is implanted in the body. The "caudal" end or part of an element of a prosthesis is to be understood as meaning the end or part of the element located in the direction of the feet of the body when the prosthesis is implanted in the body. Likewise, in this application, the "cranial direction" is to be understood as meaning the direction towards said head and the "caudal direction" is opposite the "cranial direction", the cranial and caudal directions being aligned on the same axis, the cranial-caudal axis.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias or incisional hernias (a hernia occurring through a parietal surgical scar) show themselves in the form of a bulge at the surface of the skin and are classed, for example, as umbilical or inguinal hernias, depending on where they are located.

Wall reinforcement prostheses, for example for the abdominal wall, are widely used in surgery. These prostheses are intended to treat hernias by temporarily or permanently filling a tissue defect. These prostheses are generally made from a biocompatible prosthetic textile and can have a number of shapes, for example rectangular, circular or oval, depending on the anatomical structure to which they are to adapt.

When an inguinal hernia is to be treated, it is of particular importance to take into account the anatomy of the inguinal region, in particular the presence of the iliac vessels. In addition, when the patient is a man, the spermatic cord needs to be taken into account while positioning the prosthesis. The shape of a prosthesis intended to be used for treating an inguinal hernia will be dependent on the side (right or left) of the body that is to be treated. In this view, the shape of a prosthesis for treating an inguinal hernia may be defined in relation with the position of the prosthesis once implanted in the body of a patient. For example, in an implanted configuration, a prosthesis for treating an inguinal hernia comprises a medial part, a lateral part, a caudal part, and a cranial part as defined above. A prosthesis intended to be used in the treatment of an inguinal hernia will generally have an elongate shape with a longitudinal axis substantially aligned on the medial-lateral axis of the body.

When repair of a hernia in the inguinal region is performed by pre-peritoneal placement of a prosthesis within an open surgical procedure, for example according to a transinguinal preperitoneal (TIPP) procedure, it is important to be able to locate, and to cover with the prosthesis, certain anatomical elements of the anterior wall of the abdomen, which elements may be described as follows, from the inside outwards, that is to say towards the outside of the body, and for the right-hand side of the body with reference to FIG. 1:

to the inside, the anterior retro-parietal space is limited towards the front by the rectus abdominis muscles 16, towards the rear by the peritoneum (not shown), and underneath by the upper margin of the os pubis 17;

the middle part is limited towards the front by the fascia transversalis (not shown), and the conjoint tendon, with the iliac vessels 11 below, and with the transverse muscle 18 above;

in the outer part, towards the front there is the internal orifice 19 of the inguinal canal with the elements of the spermatic cord (spermatic vessels and ductus deferens), with the psoas muscle 12 below, and with the transverse muscle 18 above.

The peritoneum is not shown in FIG. 1: it is situated between FIG. 1 and the person looking at FIG. 1. For example, an indirect inguinal hernia is a swelling of the groin caused when a portion of the peritoneum, possibly containing abdominal viscera, passes through the orifice 19 of the inguinal canal. It is necessary to protect this orifice 19 and to push the peritoneum, and possibly the abdominal viscera, back in the direction of the abdominal cavity, and place a barrier, namely a prosthesis, between the peritoneum and the orifice 19 of the inguinal canal. In other types of inguinal hernias, such as the femoral hernia or the direct hernia, the biological tissues to be protected are the illiac vessels 11 or the spermatic cord 20.

It will be noted in FIG. 1 that the elements described above are not all in the same spatial plane, but instead are arranged in an oblique arrangement from the top downwards and from the outside inwards. In the case of an inguinal hernia, the prosthesis implanted after reduction of the hernia must ensure satisfactory covering by adapting to the contours of the region and by respecting the obliqueness of the inguinal space, if possible without leaving any empty spaces.

When operating by open surgery, the surgeon has to bring the prosthesis into this inguinal region from an incision performed in the abdominal skin and the muscles and then place the prosthesis correctly with respect to all the elements described above. In order to minimize the trauma subsequent to any surgical intervention, the incision must be as small as possible, for example 4 cm long, or better only 3 cm long.

Moreover, because of the obliqueness of the inguinal region and the restricted deployment space, it can prove complicated to deploy the prosthesis and then orient it suitably with respect to the orifice of the inguinal canal or to the other organs to be protected, such as the illiac vessels or the spermatic cord. Moreover because of the specific location of the inguinal region beyond the muscles, in other words far from the incision in the abdominal skin, the surgeon has hardly any visibility at the implantation site.

The effectiveness of the prosthesis, hence the ability to minimize the risks of recurrence, depends to a large extent on how well the prosthesis is correctly spread out against the biological tissues of the inguinal region. In the present application, "biological tissues of the inguinal region" are understood as the biological tissues of the organs or elements of the inguinal region that are shown in FIG. 1 and that are intended to be protected from the peritoneum with a view to repairing the hernia, and in particular the anterior muscle wall, the orifice of the inguinal canal, the upper part of the os pubis and of Cooper's ligament, the iliac and spermatic vessels, and part of the psoas muscle.

Indeed, prostheses based on a textile are generally flexible. In order to introduce them into the abdominal incision, they are often folded up to reduce their volume. They therefore tend to form creases when introduced at the implantation site. This phenomenon may even be amplified when the prosthesis is not intended to remain permanently in the body of the patient and is therefore based on a bioresorbable textile. Indeed, bioresorbable textiles may be made from low density meshes or knit designs. The possible low density of bioresorbable textiles puts further pressure on such textiles' inherent ability to spread themselves out in an implantation site. The spreading out of textile based prosthesis, in particular of bioresorbable prosthesis, is therefore of key importance but can prove difficult, particularly when the incision completed on the skin of the patient is small and offers the surgeon poor space and visibility to manipulate and position the prosthesis.

There is therefore still the need for a prosthesis for repair of inguinal hernias that is based on a biocompatible textile, that is able, in a first configuration, to occupy a small volume so as to facilitate its introduction into the inguinal space through a small incision, and which can then be easily deployed, spread out and pressed flat against the biological tissues of the inguinal region, such that the surgeon is assured of the optimal positioning of the prosthesis.

The present invention aims to meet such a need.

A first aspect of the invention concerns a prosthesis for the repair of an inguinal hernia, of generally elongate shape defining a longitudinal axis A aligned on a medial-lateral axis and a transversal axis B aligned on a cranial-caudal axis comprising:

at least one flexible biocompatible textile of elongate shape comprising a medial end, a lateral end, a cranial part and a caudal part, said textile being delimited by a peripheral outer edge formed of a convex medial edge, a convex cranial edge, a convex lateral edge and a caudal edge, and at least one reinforcing element for said textile, said reinforcing element being in the form of a resilient frame connected to said textile and set back from the peripheral outer edge, characterized in that said frame comprises a convex cranial segment extending from the medial end of the textile to the lateral end of said textile along said convex cranial edge, a caudal segment substantially extending from the medial end of the textile to the lateral end of said textile and caudally spaced with respect to said convex cranial segment, a lateral corner segment joining together the convex cranial segment and the caudal segment in the region of the lateral end of the textile, and a folding segment configured for joining a medial end of said convex cranial segment to a point located on the caudal segment while leaving the region of the medial end of the textile free of any frame, said frame being able to adopt an unstressed configuration, in which said textile is deployed, and a stressed configuration, in which said frame is subjected to a transversal force directed towards said longitudinal axis A, and said convex cranial segment, said caudal segment and said folding segment are substantially collected together and aligned on one folding direction, said textile forming thereby at least one fold along said folding direction.

In the prosthesis of the invention, the cranial part of the textile is intended to be placed facing the anterior muscle wall, the orifice of the inguinal canal, the upper part of the os pubis and Cooper's ligament, and the caudal part of the textile is intended to be placed facing the iliac and spermatic vessels and part of the psoas muscle. The medial end of the textile is oriented in the direction of the os pubis. The prosthesis of the invention is therefore adapted for the treatment of various types of inguinal hernias, such as direct inguinal hernia, femoral inguinal hernia and indirect inguinal hernia.

As has been seen above, the specific nature of the inguinal region, which is not symmetrical, means that the orientation of the prosthesis is imperative during implantation. This is because the cranial part of the prosthesis often has a larger surface than the caudal part. It is therefore imperative that the cranial part of the prosthesis is correctly positioned facing the anterior muscle wall, the orifice of the inguinal canal, the upper part of the os pubis and Cooper's ligament, and that the caudal part of the prosthesis is correctly positioned facing the iliac and spermatic vessels and part of the psoas muscle. In this view, only one face of the prosthesis is intended to be placed facing the the biological tissues of the inguinal region, while the opposite face is intended to be placed facing the peritoneum.

The prosthesis according to the invention is able to be folded up along at least one folding direction in a very simple way, for example by pressing the frame together, in one hand, transversally in the direction of the longitudinal axis of the prosthesis. Thus, the prosthesis is capable of adopting an elongate configuration, which is very compact in the transversal direction, allowing it to pass easily through an incision of very small size, such as an incision of 3 cm long, without the aid of additional tools. The frame is sufficiently resilient to allow the prosthesis to be folded in order to enter the incision. When it emerges from the incision, the prosthesis tends to spread out automatically under the action of the frame, which tends to recover its initial configuration in the absence of the stresses from the walls of the incision. The prosthesis is capable of conforming to the anatomical structures and of remaining in place once it is positioned at the implantation site.

According to the present invention, "textile" is understood as any arrangement or assembly of biocompatible yarns, fibres, filaments and/or multifilaments, for example obtained by knitting, weaving, braiding, or non-woven.

In the present application, "biocompatible" is understood as meaning that the materials having this property can be implanted in the human or animal body.

Within the meaning of the present application, a "flexible textile" is understood as a textile that can be folded up but that does not have an inherent elasticity allowing it to spontaneously recover a spread-out configuration once it has been folded up.

Within the meaning of the present application, a "resilient frame" is understood as a frame which, for example, can be semi-rigid and has a resiliency or elasticity allowing it to be deformed under the effect of a temporary stress and allowing it to return to an initial state of rest once said stress has been removed. According to the present invention, the frame allows the textile, and therefore the prosthesis, to be pressed together in the transversal direction towards the longitudinal axis of the textile.

This step of pressing together is made easier by the specific shape of the frame. The respective shapes of the convex cranial segment, the caudal segment and the folding segment allow these segments to be able to converge together and to be aligned on one folding direction when a transversal pressure is exerted on the frame. The absence of any frame structure in the region of the medial end of the textile allows the convex cranial segment and the caudal segment to be brought close together, for example side by side or alternatively one on the top of the other, at the time of the folding of the prosthesis. The transversal volume occupied by the prosthesis is therefore reduced, making it easier to introduce the prosthesis into the incision performed by the surgeon, in the direction of the longitudinal axis of the prosthesis. As will appear from the description below, the prosthesis may further comprise a deploying element in this same region of the medial end of the textile, such deploying element being preferably separate from the frame, such deploying element helping drawing away the convex cranial segment from the caudal segment at the time the prosthesis is being deployed, such deploying element therefore further contributing to confirm to the surgeon that the prosthesis is correctly spread out.

The materials that may be suitable for producing the frame of the prosthesis according to the invention may be chosen from any biocompatible material having a certain rigidity and a certain resilience in order to meet the requirements described above.

In one embodiment, the frame is made of a bioresorbable material. In the present application, "bioresorbable" or "biodegradable" is understood to mean that the materials having this property are absorbed and/or degraded by the tissues or washed from the implantation site and disappear in vivo after a certain time, which may vary, for example, from a few hours to a few months, depending on the chemical nature of the materials.

Thus, the frame may act as a guide for the prosthesis for introducing said prosthesis into a small incision, then may act as a means of stiffening the prosthesis during the positioning and implanting of the prosthesis in order to ensure a good deployment of the prosthesis, after which it may gradually degrade when the textile has been recolonized by the surrounding cells.

For example, the bioresorbable material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. For example, the bioresorbable material can be a copolymer of polylactic acid and of polyglycolic acid.

Alternatively, the frame of the prosthesis according to the invention is made of a non-bioresorbable material chosen from among polypropylenes, polyesters such as polyethyleneterephthalates, polyamides, silicones, polyether ether ketone (PEEK), polyether ketone ketone (PEKK), polyarylether ether ketone (PAEK), polyurethanes and mixtures thereof.

In another embodiment, said frame is formed by a combination of bioresorbable material and of non-bioresorbable material.

The frame of the prosthesis according to the invention is substantially set back from the peripheral outer edge of the textile. Thus the frame may have an outer perimeter lower than that of the peripheral outer edge of the textile. In other words, the peripheral outer edge of the textile can extend beyond the frame by a certain distance which may vary, depending on the location (medial, cranial, lateral or caudal) of the contemplated edge. For example, this distance can be greater than or equal to 1 mm. The frame will therefore generally have smaller dimensions than those of the peripheral outer edge of the textile.

The shape of the frame makes it possible to easily press together and/or fold the prosthesis and align it on the folding direction, which may be aligned on longitudinal axis A. The absence of any frame in the region of the medial end of the textile allows the textile to be folded easily.

In the prosthesis of the invention, the caudal segment of the frame may serve as a positioning guide for the surgeon, this caudal segment preferably having to be placed in the inguinal region at the intersection of the parietal and vascular planes to permit optimal positioning of the prosthesis. In one embodiment of the invention, said caudal segment may form a fold of the textile, said fold causing said caudal part of said textile to form naturally an angle to the plane of said cranial part of said textile. Thus, the caudal segment may give the textile a three-dimensional shape, similar to the anatomy of the inguinal region, by forming a fold in the textile, in such a way that the caudal part of the textile tends naturally to form an angle with the cranial part of said textile, this angle corresponding to the angle formed anatomically by the intersection of the parietal and vascular planes.

In embodiments, said caudal segment is concave. Such a shape allows an easy pressing of the frame and therefore of the prosthesis, and a significant reduction of the volume occupied by the prosthesis in the transversal direction. In addition, the concavity of the caudal segment confers to the caudal part of the textile an undulated and anatomical developed shape for matching the general shape of the lower inguinal structures, especially the spermatic and iliac vessels and the psoas muscle.

In embodiments, the folding segment joins the medial end of said convex cranial segment to a medial end of the caudal segment. For example, the folding segment has a U shape extending towards a center of the textile. In such embodiments, when pressing the frame transversally, the two legs of the U of the folding segment converge together with the convex cranial segment and the caudal segment, allowing a significant reduction of the volume occupied by the prosthesis in the transversal direction.

In one embodiment, said frame is continuous. Thus, the step of pressing the prosthesis together, by pressing the frame together towards the longitudinal axis of the prosthesis, does not create any projecting elements that could potentially perforate and damage the tissues. By virtue of its nature and its shape, the frame only has rounded and atraumatic outer contours.

In embodiments, at least a part of said frame, for example at least a part of the caudal segment, has substantially the structure of a flat band forming undulations substantially in the plane of said textile. Such undulations allow a good conformability of the prosthesis in general, and a good flexibility to the caudal segment in particular at the intersection of the parietal and vascular planes. Such undulations can expand and contract to further confer a greater flexibility to the frame. In addition, such undulations confer a good resistance to folding to the prosthesis.

In embodiments, said frame further comprises a caudal extension located on the caudal segment and extending in the caudal direction toward the caudal edge of the textile. The caudal extension helps deploying the caudal part of the textile once the prosthesis is implanted. This caudal extension helps spreading out the caudal part of the textile on the biological tissues it is intended to cover, namely the iliac and spermatic vessels and part of the psoas muscle.

The frame of the prosthesis according to the invention is connected to said textile. For example, the frame can be fixed to the textile by sewing, ultrasonic welding, or else by adhesive bonding or moulding.

In one embodiment, the frame of the prosthesis according to the invention is moulded over the textile. Thus, the frame is connected to the textile by injection moulding of one or more thermoplastic or thermosetting biocompatible materials. For example, the mould of an injection-moulding machine is equipped with an insert gate in which the textile is held. One or more thermoplastic or thermosetting biocompatible materials are then heated to their melting point and injected into the mould, the latter having one or more channels of the shape desired for the frame. The holding of the textile, the precision of the injection volume and the choice of the injection parameters make it possible to obtain a frame without material loss, without flash and with good surface evenness. Such a method allows the frame to be embedded in the textile in a particularly effective and lasting way.

In one embodiment, the frame is obtained by moulding a copolymer of polylactic acid and of polyglycolic acid over the textile.

In embodiments, the lateral corner segment is linked to the convex cranial segment and to the caudal segment via two respective hinge points allowing the lateral region of the textile to be folded onto the remaining part of the textile. Such embodiments allow reducing the volume occupied by the prosthesis in the longitudinal direction before introduction of the prosthesis in the incision and to the implantation site.

In embodiments, the prosthesis further comprises a deploying element located in the region of the medial end of the textile, for drawing away said convex cranial segment from said caudal segment when said transversal force is released and said textile is being deployed. The deploying element is preferably separate from the frame and may be under the form of one or several teeth located between the medial end of the convex cranial segment and the medial end of the caudal segment. The deploying element helps restoring the distance existing between the medial end of the convex cranial segment and the medial end of caudal segment when the prosthesis is in a spread out configuration. The deploying element therefore contributes to confirming to the surgeon that the prosthesis has been correctly deployed. In particular, the deploying element may be formed of the same material as that forming the frame. The deploying element may also be bioresorbable or not. It may be moulded on the textile.

In embodiments, the prosthesis further comprises a grasping element capable of cooperating with a part of a grasping tool so as to temporarily couple said prosthesis to said tool. The presence of a grasping element allows the prosthesis to be easily grasped by a part of a tool conventionally used in surgery, for example one of the jaws of a pair of forceps. Preferably, the grasping element is located in the region of the medial end of the textile. Indeed, as will appear from the description below, the prosthesis of the invention is intended to be inserted in the abdominal incision via its medial end. The presence of a grasping element in the region of the medial end of the textile allows the surgeon to couple the prosthesis to the grasping tool while completing a global distal movement of insertion of the prosthesis in the incision, with the medial end of the prosthesis drawn forward by the grasping tool and the lateral end of the prosthesis naturally following the movement.

The grasping element may have any shape adapted for receiving a part of a grasping tool, such as a jaw of a pair of forceps in temporary engagement. For example, the grasping element is a loop or a hook. The grasping element may be made of the same material as that of the frame. The grasping element may also be bioresorbable or not. It may be moulded on the textile.

The textile of the prosthesis according to the invention has a generally elongate shape, for example oval or elliptic. The textile can have another initial shape and can then be cut to such an elongate shape, in particular to a shape adapted to the defect, for example the hernia defect of the inguinal region, that is to be treated. In particular, the shape of the textile of the prosthesis of the invention comprises a part capable of efficiently covering the anterior muscle wall, the orifice of the inguinal canal, the upper part of the os pubis and Cooper's ligament, and a part capable of covering efficiently the iliac vessels and spermatic vessels and part of the psoas muscle. The textile is delimited by a peripheral outer edge formed of a convex medial edge, a convex cranial edge, a convex lateral edge and a caudal edge. The caudal edge may be flat or convex. Preferably, the caudal edge is convex in order to optimize the covering of the iliac vessels and spermatic vessels and part of the psoas muscle. As such, the general shape of the peripheral outer edge is preferably convex.

The textile may be bioresorbable, permanent or partially bioresorbable. In embodiments, the textile is bioresorbable. Bioresorbable textiles may be made from low density meshes or knit designs. In embodiments, for example when the prosthesis is not intended to remain permanently in the body of a patient, both the frame and the textile are bioresorbable. For example, the frame is bioresorbable in a time frame comparable to the textile. The shape and nature of the frame of the prosthesis of the invention allow providing a prosthesis based on a low density bioresorbable textile capable of offering sufficient strength for performing its repair function and sufficient rigidity for being efficiently manipulated while at the same time limiting the amount of foreign material implanted.

In one embodiment, the textile is a mesh.

Within the meaning of the present application, a "mesh" is understood as a textile, as defined above, which is openworked, that is to say provided with pores that favour recolonization of tissue. It is sufficiently flexible to be folded up at the time of introduction into the abdominal cavity. The mesh can be made from a layer of textile or several layers of textile. Such meshes are well known to a person skilled in the art.

In one embodiment of the invention, the mesh is a knit. By virtue of the meshwork of the knit, it is possible to obtain openworked faces that promote cell recolonization after implantation. The knit can be two-dimensional or three-dimensional.

Within the meaning of the present application, a two-dimensional knit is understood as a knit having two opposite faces linked to each other by meshes but devoid of a spacer giving it a certain thickness: such a knit can be obtained, for example, by knitting yarns on a warp knitting machine or raschel knitting machine using two guide bars. Examples of knitting two-dimensional knits suitable for the present invention are given in the document WO2009/071998.

According to the present application, a three-dimensional knit is understood as a knit having two opposite faces linked to each other by a spacer that gives the knit a significant thickness, said spacer itself being formed from additional linking yarns in addition to the yarns forming the two faces of the knit. Such a knit can be obtained, for example, on a double-bed warp knitting or raschel knitting machine using several guide bars. Examples of knitting three-dimensional knits suitable for the present invention are given in the documents WO99/05990, WO2009/031035 and WO2009/071998.

In embodiments of the invention, one face of the textile may be covered by a non-stick coating. Such a non-stick coating makes it possible in particular to avoid the formation of undesired and serious post-surgical fibrous adhesions. Within the meaning of the present application, "non-stick" is understood as a smooth and non-porous biocompatible material or coating that does not offer space for cell recolonization and that preferably promotes the growth of peritoneum.

Another aspect of the present invention is a method by which a prosthesis as described above is conveyed to an implantation site of the inguinal region during an open surgery procedure, said method comprising the following steps:

an incision of size ranging from 3 to 4 cm is completed on the abdominal skin, the above prosthesis is pressed together and/or folded upon itself, by applying a transversal pressure on the frame, so that said textile forms a fold along the folding direction, and said convex cranial segment, said caudal segment and said folding segment are substantially collected together, for example side by side or one on top of the other, and aligned on one folding direction, the medial end of the prosthesis is approached towards the incision, optionally by temporarily coupling the prosthesis with a grasping tool when a grasping element is present, and the folded prosthesis is fully introduced in the incision and conveyed to the implantation site in the inguinal region, the pressure exerted on the frame is released and the prosthesis is automatically deployed by means of the frame coming back to its unstressed configuration, and optionally with the help of the deploying element and/or of the caudal extension of the frame, and/or with the surgeon's finger.

The prosthesis is fitted in place facing the surrounding biological tissues, by positioning the cranial part of the textile facing the anterior muscle wall, the orifice of the inguinal canal, the upper part of the os pubis and Cooper's ligament, and the caudal part of the textile facing the iliac and spermatic vessels and part of the psoas muscle, if appropriate with the aid of the caudal segment, by placing the latter at the intersection of the parietal and vascular planes.

The automatic return of the frame to its initial configuration contributes to an initial deployment of the prosthesis at the implantation site. Because of the restricted space and visibility at the implantation site, the surgeon may further need to finalize the deployment of the prosthesis with his fingers and/or with the deploying element and caudal extension when present. Indeed, when operating in the inguinal region via an open surgery procedure, the surgeon is unable to see the implantation site with his eyes. He can only feel the surrounding biological tissues by touching them with his fingers. In this context, the presence and shape of the frame helps the surgeon feel and evaluate the geometry of the prosthesis with his fingers and further helps him determine the best position of the prosthesis with respect to the surrounding organs for a most efficient spreading-out of the latter at the implantation site. In embodiments where the lateral corner segment is linked to the convex cranial segment and to the caudal segment via two respective hinge points, the lateral region of the textile is folded onto the remaining part of the textile before the step of introducing the prosthesis into the incision. In such a case, the global volume occupied by the prosthesis at the time it is introduced in the incision is greatly reduced. Indeed, this volume is first reduced in the transversal direction because of said convex cranial segment, said caudal segment and said folding segment being substantially collected together aligned on one folding direction. In addition, this volume is also reduced in the longitudinal direction because the the lateral region of the textile is folded onto the remaining part of the textile.

BRIEF DESCRIPTION OF THE DRAWINGS

The advantages of the present invention will become clearer from the following detailed description and from the attached drawings in which.

DETAILED DESCRIPTION OF THE INVENTION

FIGS. 2-5 show embodiments of a prosthesis 1 according to the invention. The prostheses 1 of these figures all comprise a biocompatible textile 2 and a reinforcing element in the form of a frame 3.

Figure 9:
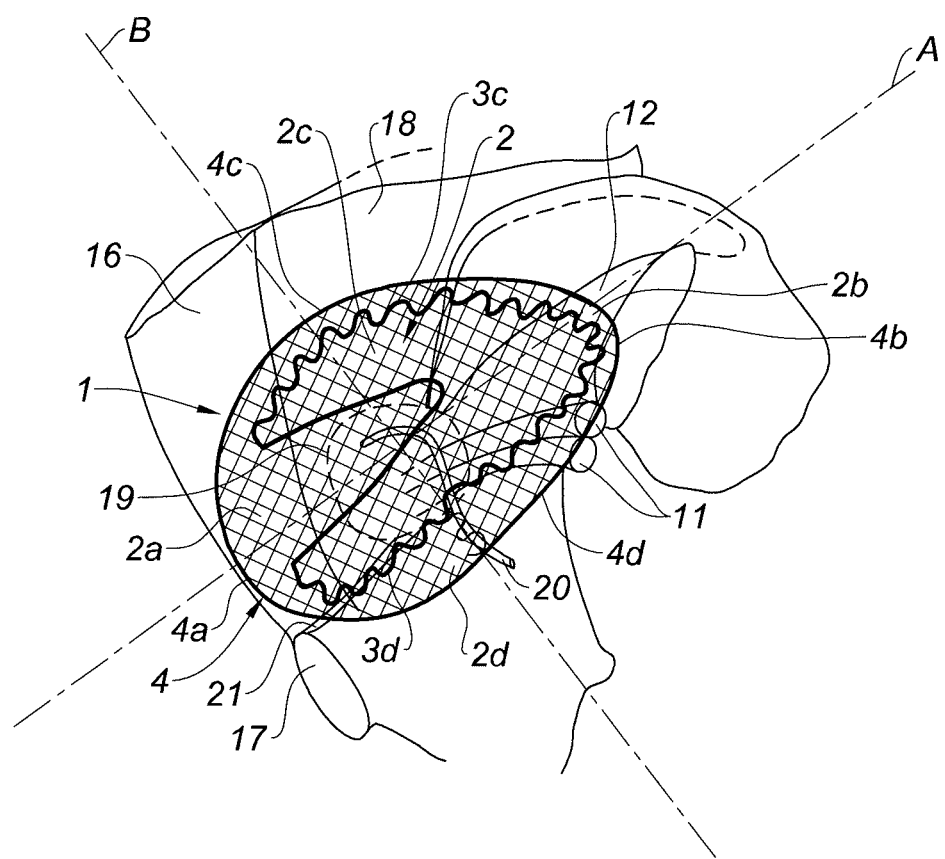
FIG. 9 is a perspective view of the prosthesis of FIG. 4 once implanted and positioned with respect to the anatomical elements of the extraperitoneal inguinal region, on the right-hand side of a human body, seen from the inside outwards, that is to say towards the outside of the body.

As will be clear from FIGS. 2-5, the textile 2 has a generally elongate shape, similar to an oval or egg shape, defining a longitudinal axis A and a transversal axis B. With reference to FIG. 9, in an implanted configuration of the prosthesis 1 of FIG. 4, the longitudinal axis A is aligned on the medial-lateral axis of a human body and the transversal axis B is aligned on the cranial-caudal axis of a human body.

Figure 2:
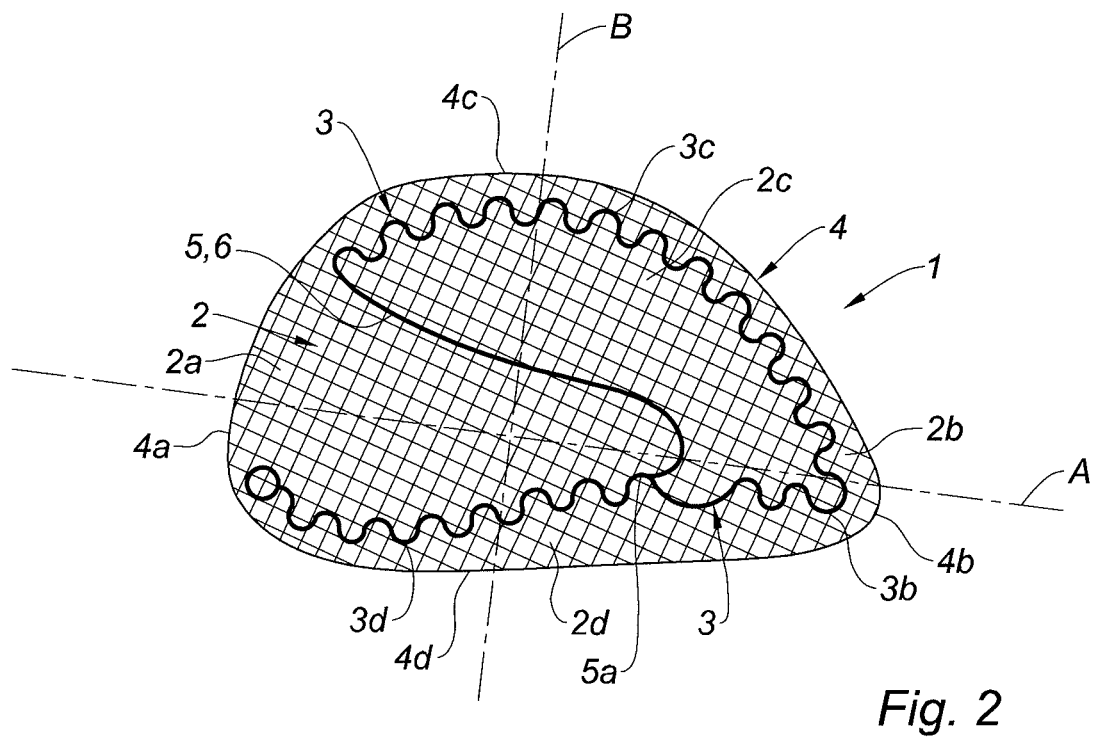
FIG. 2 is a top view of a first embodiment of the prosthesis of the invention.
Figure 3:
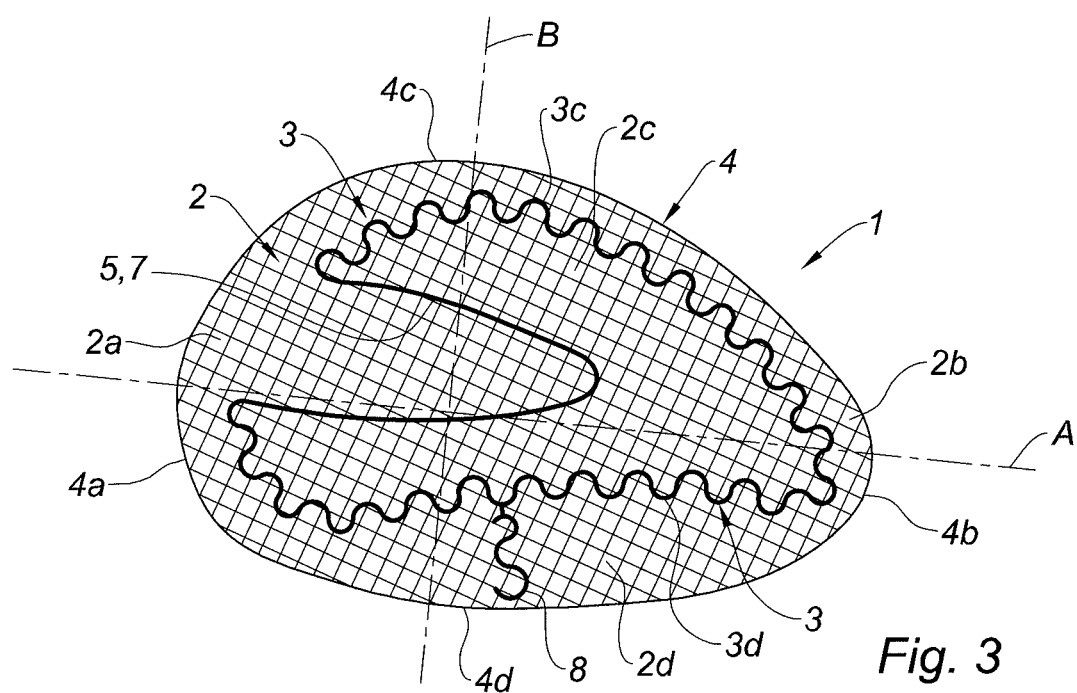
FIG. 3 is a top view of a second embodiment of the prosthesis of the invention.
Figure 4:
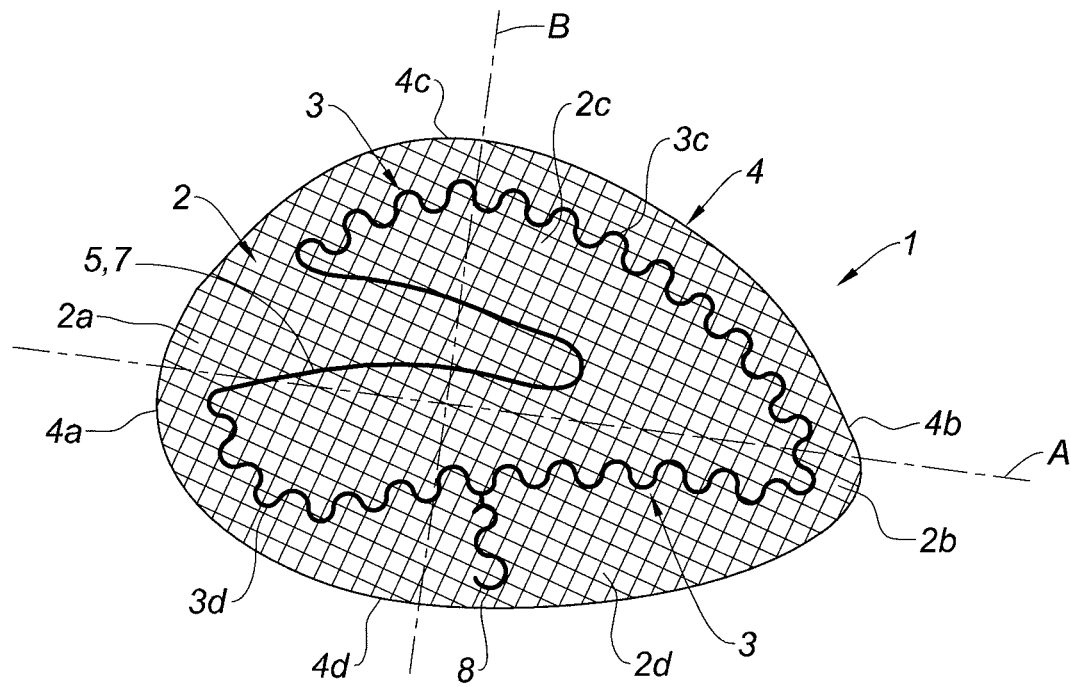
FIG. 4 is a top view of a third embodiment of the prosthesis of the invention.
Figure 5:
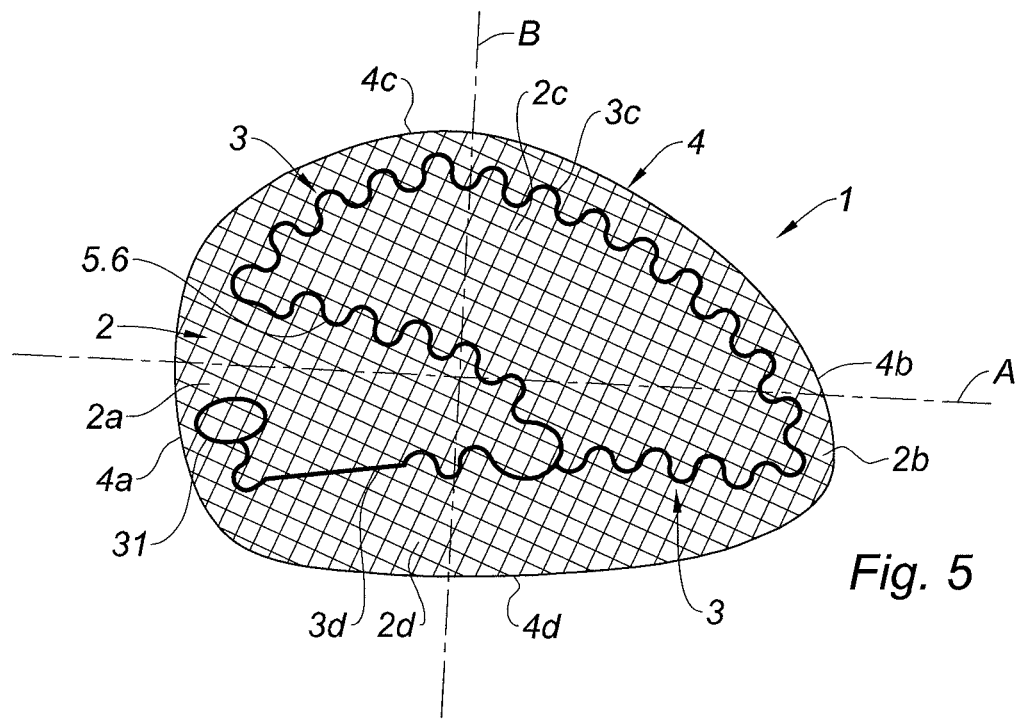
FIG. 5 is a top view of a fourth embodiment of the prosthesis of the invention.

The textile 2 is thus delimited by a peripheral outer edge 4. The textile 2 comprises a medial end 2a, a lateral end 2b, a cranial part 2c and a caudal part 2d. With reference to FIGS. 2 and 5, the peripheral outer edge 4 is formed of a convex medial edge 4a, a convex cranial edge 4c, a convex lateral edge 4b and a rather flat caudal edge 4d. With reference to FIGS. 3 and 4, the peripheral outer edge 4 is formed of a convex medial edge 4a, a convex cranial edge 4c, a convex lateral edge 4b and a convex caudal edge 4d, and is therefore globally convex.

In the examples shown, the textile 2 has the general shape of the section of an egg by a longitudinal plane. Such a shape is particularly suitable for the repair of an inguinal hernia. In particular, as appears from FIG. 9, the cranial part 2c of the textile 2 is designed and shaped so as to efficiently cover the anterior muscle wall (16, 18), the upper part of the os pubis 17 and Cooper's ligament 21, while the caudal part 2d of the textile 2 is designed and shaped so as to cover efficiently the iliac vessels 11 and spermatic vessels 20 and part of the psoas muscle. In this view, the cranial part 2c is generally larger than the caudal part 2d. In addition, the medial end 2a has a rounded configuration that makes it capable of overlying and covering the orifice 19 of the inguinal canal. The lateral end 2b has also a rounded configuration, but of smaller size than the medial end 2a, as it is located away from the orifice 19 of the inguinal canal in an area where less foreign material is needed and desired.

In other embodiments, the textile 2 could have a globally oval or rectangular shape or could be protean if the shape in question is generally elongate and is adapted to cover the hernia defect in the inguinal region as explained above.

The textile 2 is made up of an arrangement of biocompatible filaments, such as a knit, a woven or a nonwoven. Preferably, as is shown in FIGS. 2-5, the textile 2 is in the form of a mesh, that is to say it has openings for better tissue integration. For example, the textile 2 can be a two-dimensional or three-dimensional knit. Such textiles in the form of meshes or knits are well known to a person skilled in the art and are not described in any greater detail here.

The textile 2 can be bioresorbable, permanent or partially bioresorbable. As will become clear from the description below, the textile 2 is sufficiently flexible to be folded up, in particular at the time of introduction of the prosthesis into the abdominal incision, along at least one folding direction. In general, however, the textile 2 does not have an inherent elasticity allowing it to spontaneously recover a spread-out configuration once it has been folded up. The textile 2 can be supplied in the form of a band, which one cuts to the dimensions of the defect to be treated.

Referring again to FIGS. 2-5, and as will become clear on reading the description below, the frame 3 acts as an element reinforcing the textile 2 in order to stiffen the latter and keep it in its generally elongate shape, as a tool for guiding the prosthesis 1 at the time of its introduction into the abdominal incision, and as a tool for assisting in the deployment of the prosthesis 1 when the prosthesis 1 reaches the implantation site. For this purpose, the frame 3 is connected to the textile 2 and has an elasticity allowing it to be deformed under the effect of a temporary stress and allowing it to return to an initial state of rest once said stress has been removed.

The frame 3 is connected to the textile 2. It can be attached to the textile 2 by means of a seam, or else by means of an ultrasonic weld, by adhesive bonding, or by injection moulding.

In one embodiment, the frame 3 is connected to the textile 2 by injection moulding of one or more thermoplastic or thermosetting biocompatible materials. Such an embodiment makes it possible to secure the fixing of the frame to the textile in a particularly effective manner and to produce the prostheses according to the invention at an industrial scale.

In the injection moulding technique, a mould is formed in which, for example, there is a cavity defining a contour which corresponds to the contour of the frame that is to be obtained. The textile is held in an insert gate of the mould. The thermoplastic material used to produce the frame, for example a copolymer of polylactic acid and of polyglycolic acid, is heated and injected into the cavity using an injection moulding machine.

After the injection step, the mould is opened and the prosthesis 1 is withdrawn from the mould. Such a method allows the textile to be "embedded" in the part moulded over it. Thus, the frame 3, which is the overmoulded part, is connected to the textile, without any risk of its coming loose or fragmenting. The frame 3 is slightly set back from the peripheral convex outer edge 4.

With reference to FIGS. 2-5, the frame 3 comprises a first segment which is a convex cranial segment 3c and which extends from the medial end 2a of the textile 2 to the lateral end 2b of the textile 2 substantially parallel to the convex cranial edge 4c. The frame 3 further comprises a second segment which is a caudal segment 3d substantially extending from the medial end 2a of the textile 2 to the lateral end 2b of the textile 2 and caudally spaced with respect to the convex cranial segment 3c. The frame 3 further comprises a lateral corner segment 3b joining together the convex cranial segment 3c and the caudal segment 3d in the region of the lateral end 2b of the textile 2.

Eventually, always with reference to FIGS. 2-5, the frame 3 comprises a last segment which is a folding segment 5 configured for joining a medial end of the convex cranial segment 3c to a point 5a located on the caudal segment 3d. As appears from FIGS. 2-5, the frame 3 encompasses all these segments, convex cranial segment 3c, lateral corner segment 3b, caudal segment 3d and folding segment 5, in a continuous way. The frame 3 is therefore continuous. As also appears from FIGS. 2-5, the shape of the frame 3 leaves the region of the medial end 2a of the textile 2 free of any frame structure.

More particularly, with reference to FIGS. 2 and 5, the folding segment 5 is a globally linear segment 6 joining the medial end of the convex cranial segment 3c to a point 5a located in the lateral region of the caudal segment. With reference to FIG. 5, the linear segment 6 is under the form of a flat band forming undulations.

With reference to FIGS. 3 and 4, the folding segment 5 joins the medial end of said convex cranial segment to a medial end of the caudal segment and the folding segment 5 is a U shaped body 7 extending towards a center of the textile.

Thus, in the examples shown in FIGS. 2-5, the caudal segment 3d and the folding segment (5, 6), or alternatively the folding segment (5, 7) on its own, define a sort of mouth of the frame 3 in the medial end 2a of the textile 2. The presence of this mouth allows an easy folding of the textile 2 and therefore of the prosthesis 1 when a pressure, such as the force F shown on FIG. 6 in relation with the prosthesis 1 of FIG. 4, is exerted on the frame 3. This pressure allows reducing the volume occupied by the prosthesis 1 in the transversal direction, as will be clear from comparison of FIGS. 4 and 6 showing the same prosthesis 1 respectively in its spread out configuration and in its compressed configuration.

In addition, because of the frame 3 being continuous, the step of pressing the prosthesis 1 together, by pressing the frame 3 together towards the longitudinal axis A of the prosthesis 1, does not create any projecting elements that could potentially perforate and damage the tissues. By virtue of its nature and its shape, the frame only has rounded and atraumatic outer contours.

Figure 6:
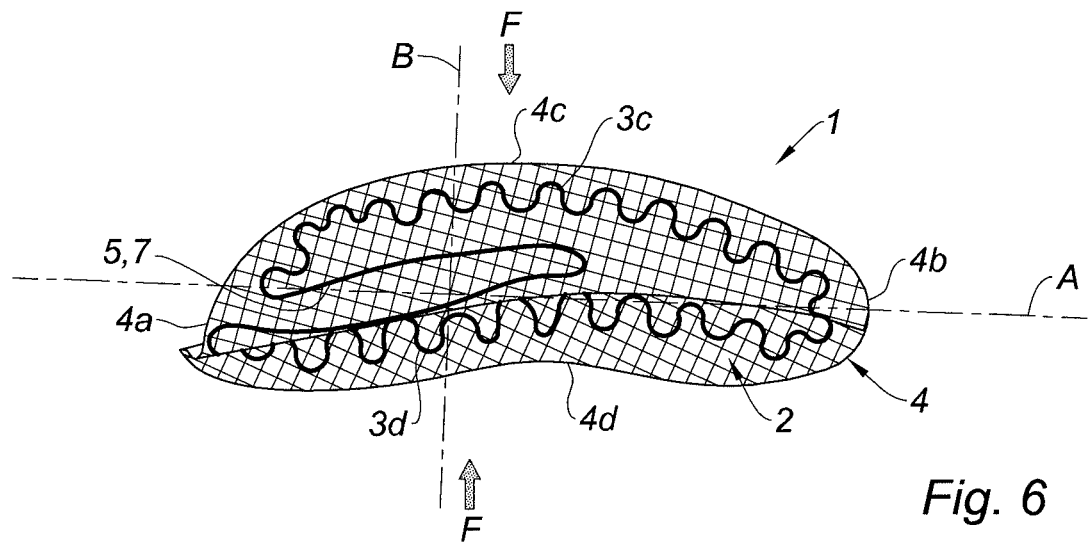
FIG. 6 is a top view of the prosthesis of FIG. 4 in a compressed configuration.

In particular, the frame 3 has a structure, in other words a shape, and a nature, in other words a material, giving it an elasticity such that it is able to adopt a first, unstressed configuration in which the textile 2 and the prosthesis 1 are deployed and spread out as shown in FIG. 2, and a second, stressed configuration in which the frame 3 is subjected to a transversal force directed towards said longitudinal axis A and the convex cranial segment 3*c*, the caudal segment 3*d* and the folding segment 5 are substantially collected together and aligned on one folding direction, the textile 2 forming thereby at least one fold along the folding direction, as shown on FIG. 6 in relation with the prosthesis 1 of FIG. 4.

As shown on FIGS. 2-5, at least a part of the frame 3 has substantially the structure of a flat band forming undulations substantially in the plane of the textile 2. Such undulations allow a good conformability of the prosthesis. Such undulations further confer a spring behavior to the frame 3. In addition, such undulations confer a good resistance to folding to the prosthesis 1.

As shown on FIGS. 2-4, the caudal segment 3*d* may be concave. As appears from FIG. 9, the caudal segment 3*d* may form the frontier between the cranial part 2*c* and the caudal part 2*d* of the textile 2.

For example, the cranial part 2*c* is substantially planar and large enough so as to cover the anterior muscle wall (16, 18), the orifice 19 of the inguinal canal, the upper part of the os pubis 17 and Cooper's ligament 21. The concavity of the caudal segment 3*d* confers to the caudal part 2*d* of the textile 2 an undulated and anatomical developed shape for matching the general shape of the lower inguinal structures, especially the spermatic and iliac vessels and the psoas muscle, as will be seen from FIG. 9. The concavity of the caudal segment 3*d* gives the caudal part 2*d* a curved shape, this caudal part 2*d* thus forming with the cranial part 2*c* an angle corresponding to the angle formed by the parietal and vascular planes at the intersection thereof in the inguinal region of a human body. Thus, the cranial part 2*c* and the caudal part 2*d* are asymmetrical, which means that a left-hand prosthesis or right-hand prosthesis will be used depending on which side the hernia to be treated is located. As is shown in FIG. 9, the prosthesis 1 of FIG. 4 is a prosthesis for the repair of an inguinal hernia on the right-hand side of a patient. A prosthesis suitable for the repair of an inguinal hernia on the left-hand side of a patient would have a shape the mirror image of the prosthesis 1 of FIG. 4.

With reference to FIGS. 3 and 4, the frame 3 further comprises a caudal extension 8 located on the caudal segment 3*d* and extending in the caudal direction substantially up to the caudal edge 4*d* of the textile 2. The caudal extension 8 helps deploying the caudal part 2*d* of the textile 2 once the prosthesis 1 is implanted, as shown on FIG. 9. This caudal extension 8 helps spreading out the caudal part 2*d* of the textile on the biological tissues it is intended to cover, namely the iliac and spermatic vessels and part of the psoas muscle.

Figure 7:
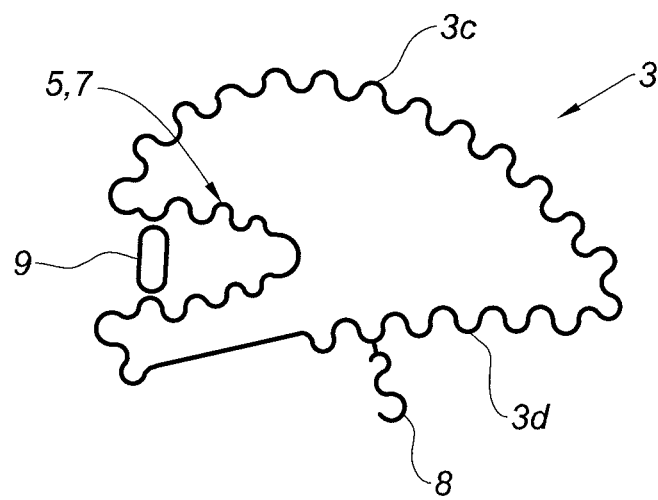
FIG. 7 is a top view of another embodiment of the frame of the prosthesis of the invention.
Figure 8:
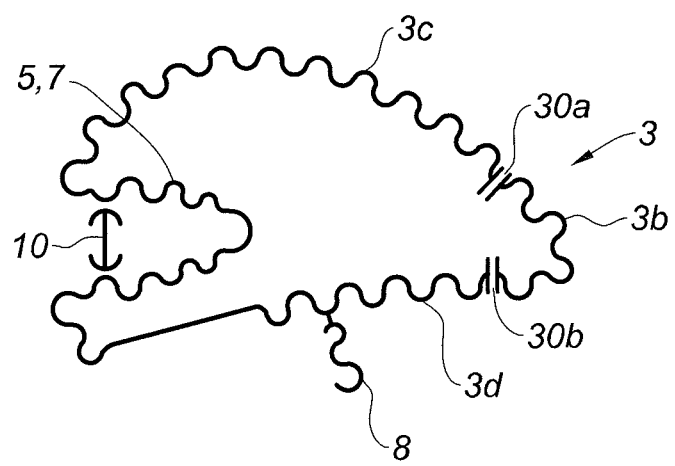
FIG. 8 is a top view of another embodiment of the frame of the prosthesis of the invention.

With reference to FIGS. 7 and 8 are shown frames 3 suitable for the prosthesis of the invention and further comprising a deploying element, such as a tooth 9 (FIG. 7) or an arrow 10 (FIG. 8), located in the region of the medial end of the textile (not shown). The deploying element (9, 10) serves for drawing away the convex cranial segment 3*c* from the caudal segment 3*d* when the transversal force is released and the textile is being deployed once the prosthesis has reached the implantation site. More particularly, the deploying element (9, 10) is located in the inside of the mouth defined by the folding segment 5 and optionally the caudal segment 3*d* as described above, in order to restore the width of said mouth in the process of redeployment of the prosthesis. The deploying element (9, 10) is preferably separate from the frame 3 so that it does not impinge on the coming closer together of the convex cranial segment 3*c* and of the caudal segment 3*d* at the time of the folding of the prosthesis. The deploying element (9, 10) may be formed of the same material as that forming the frame 3. The deploying element (9, 10) may also be bioresorbable or not. It may be moulded on the textile.

With reference to FIG. 8, the lateral corner segment 3*b* is linked to the convex cranial segment 3*c* and to the caudal segment 3*d* via two respective hinge points (30*a*, 30*b*). These two hinge points (30*a*, 30*b*) allow the lateral region of the textile (not shown) to be folded onto the remaining part of the textile. Such embodiments allow reducing the volume occupied by the prosthesis in the longitudinal direction before introduction of the prosthesis in the incision and to the implantation site.

With reference to FIG. 5, the prosthesis 1 further comprises a grasping element under the form of a loop 31 located at the medial end of the caudal segment 3*d*. The loop 31 is capable of cooperating with a part of a grasping tool, such as a jaw of a pair of forceps (not shown) so as to temporarily couple the prosthesis 1 to the tool. For example, the part of the textile 2 located within the loop 31 may be cut so that the distal end of the jaw traverses the textile 2 and grasps the prosthesis 1. The presence of the loop 31 in the region of the medial end of the textile 2 allows the surgeon to couple the prosthesis 1 to the grasping tool at the time he completes a global distal movement for insertion of the prosthesis in the abdominal incision, with the medial end of the prosthesis 1 drawn forward by the grasping tool and the lateral end of the prosthesis naturally following the movement. Once the prosthesis 1 is conveyed to the implantation site, the surgeon simply pulls proximally on the grasping tool which naturally uncouples from the prosthesis 1. In other embodiments not shown, the loop 31 could be replaced by a hook. The loop 31 may be made of the same material as that of the frame 3, and may be bioresorbable or not. It may be moulded on the textile 2.

The prosthesis of the invention ensures that all of the anatomical elements described above are covered, without leaving empty spaces that could possibly cause a recurrence. In particular, the region around the iliac and spermatic vessels is particularly well protected. This therefore avoids one of the main causes of secondary hernias, which can be even more difficult to treat on account of the deterioration of the anatomical structures that has been caused by the earlier hernia.

The use and the implantation of the prosthesis according to the invention will now be described with reference to the treatment of an inguinal hernia on the right-hand side of a patient by an open surgery procedure using the prosthesis 1 from FIGS. 4 and 6.

Figure 1:
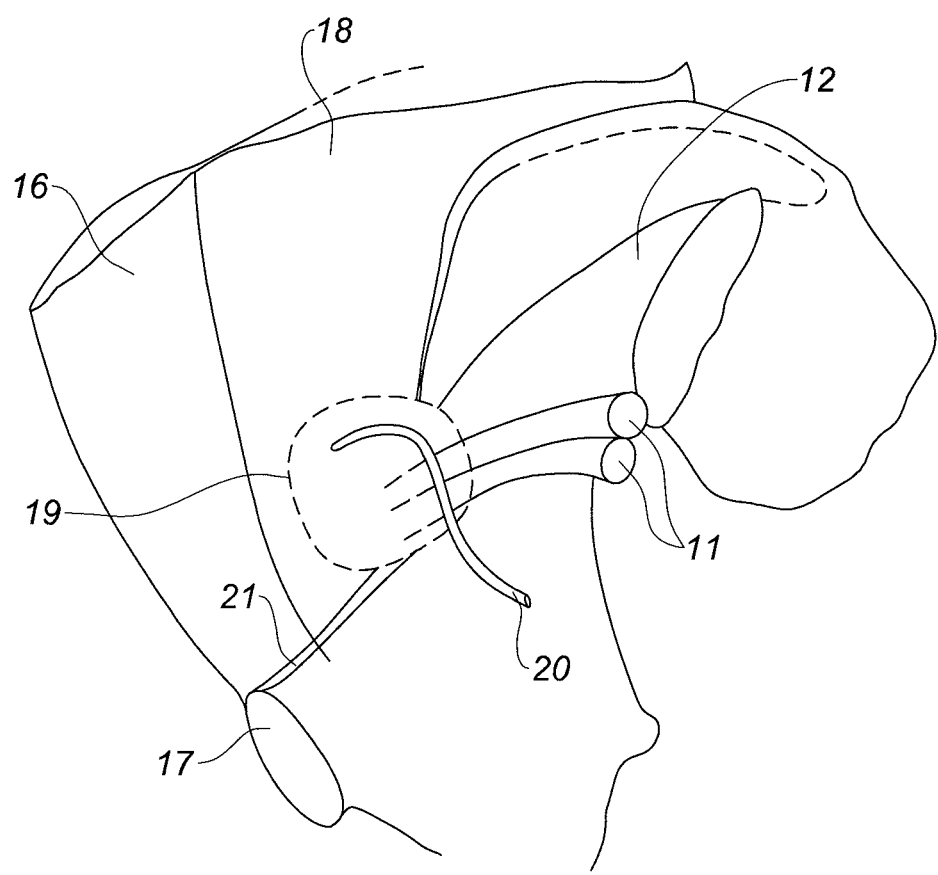
FIG. 1 is a perspective view of the inguinal region on the right-hand side of a human body.

The perspective views in FIGS. 1 and 9 show, on the one hand, the anatomical elements of the extraperitoneal inguinal region on the right-hand side of a human body, seen from the inside outwards, that is to say towards the outside of the body as has been described above, and, on the other hand, a view of the positioning of the prosthesis according to the present invention in relation to these elements once it has been implanted.

It can be clearly seen in FIG. 1 that the inguinal region is particular in that the elements described above are not all in the same spatial plane, but instead are arranged in an oblique arrangement from the top downwards and from the outside inwards. In the case of an inguinal hernia, the prosthesis implanted after reduction of the hernia must ensure satisfactory covering by adapting to the contours of the region and by respecting the obliqueness of the inguinal space.

The surgeon is provided with a prosthesis 1 of FIG. 4. The surgeon applies a transversal pressure on the frame 3 of the prosthesis 1 as shown by arrows F on FIG. 6. Under this pressure, the convex cranial segment, the caudal segment 3*d* and the folding segment 5 are collected together, for example side by side or one on top of the other(s), and become aligned on a main direction, herein called the folding direction, which is the direction of the longitudinal axis A on FIG. 6 in the present example. In other embodiments, the folding direction may differ slightly or substantially from the direction defined by the longitudinal axis A. As appears from FIG. 6, the volume occupied by the prosthesis 1 in its compressed configuration in the transversal direction is greatly reduced compared with the volume occupied by the same prosthesis 1 in its spread out configuration as shown on FIG. 4. For example, the prosthesis 1 may have a width of 10 cm measured along the transversal direction in its spread out configuration, and a width of only 2.5 cm measured along the transversal direction in its compressed configuration.

In embodiments where the lateral corner segment is linked to the convex cranial segment and to the caudal segment via two respective hinge points (see FIG. 8), the lateral region of the textile is folded onto the remaining part of the textile before the step of introducing the prosthesis into the incision. In such a case, the global volume occupied by the prosthesis at the time it is introduced in the incision is greatly reduced. Indeed, this volume is first reduced in the transversal direction because of said convex cranial segment, said caudal segment and said folding segment being substantially collected together and aligned on one folding direction. In addition, this volume is also reduced in the longitudinal direction because the the lateral region of the textile is folded onto the remaining part of the textile.

Once the prosthesis is folded in a compressed configuration, the surgeon then approaches the medial end of the prosthesis 1 towards an incision he has previously performed in the abdominal skin of the patient and he introduces the folded prosthesis 1 into said incision. Because the volume of the prosthesis 1 is reduced in its compressed configuration, the incision may show small dimensions, such as 3 or 4 cm long. By virtue of its elongate compact shape, and the rigidity conferred on it by the presence of the frame 3, the prosthesis 1 also easily enters the incision.

The surgeon pushes on the lateral end of the prosthesis 1 in the direction of the folding direction in order to deliver the prosthesis to the implantation site in the inguinal region.

Once the prosthesis 1 is at the implantation site, namely in the inguinal region as described with reference to FIGS. 1 and 9, the prosthesis 1 automatically deploys under the effect of the frame 3 coming back to its initial shape. The textile 2 and therefore the prosthesis 1 are perfectly deployed and spread out. The prosthesis 1 is then ready to be positioned opposite a hernia defect to be treated, without any risk of folds forming in the textile 2. The risks of adherence or insertion of surrounding organs in such folds are thus very much limited.

The surgeon fits the prosthesis 1 in place facing the surrounding biological tissues, by positioning the cranial part 2*c* of the textile 2 facing the anterior muscle wall, the orifice of the inguinal canal, the upper part of the os pubis 17 and Cooper's ligament 21, and the caudal part 2*d* of the textile facing the iliac and spermatic vessels 11 and part of the psoas muscle, if appropriate with the aid of the caudal segment 3*d*, for example by placing the latter at the intersection of the parietal and vascular planes. As explained above, the surgeon finalizes the correct spreading-out and positioning of the prosthesis by feeling the frame with his fingers and optionally with the help of the deploying element and caudal extension when present.

When the prosthesis 1 is implanted as shown on FIG. 9, the cranial part 2*c* rests on the anterior muscle wall (especially the rectus abdominis muscle 16 and transverse muscle 18), the upper end of the os pubis and part of Cooper's ligament 21. The caudal part 2*d* conforms almost completely, without leaving any appreciable spaces, to the iliac and spermatic vessels 11 and the psoas muscle 12, and the caudal segment 3*d* is placed at the intersection of the parietal and vascular planes. The ductus deferens 20 is also covered and therefore protected.

The prosthesis 1 according to the invention remains in place by itself, particularly on account of its three-dimensional shape, since the caudal segment 3*d* takes up a position at the intersection of the parietal and vascular planes. This allows the prosthesis 1 to follow the changes in the relative position of the various anatomical elements of the inguinal region, which changes result from the normal movement of the abdominal muscles of the subject, but without its moving away from the implantation region.

The prosthesis according to the invention can thus be easily introduced into a small incision, for example an incision of 3 or 4 cm long, without requiring the help of an additional tool. By virtue of its nature and its structure, the frame of the prosthesis according to the invention acts as a reinforcing element for the textile and stiffens the prosthesis, as an element for guiding and transporting the prosthesis into an incision of particularly small diameter, and also as a tool for assisting in the automatic and perfect spreading-out of the prosthesis at the moment when the prostheses reaches the implantation site.

What is claimed is:

1. A prosthesis for the repair of an inguinal hernia, of generally elongate shape defining a longitudinal axis aligned on a medial-lateral axis and a transversal axis aligned on a cranial-caudal axis comprising:
    at least one flexible biocompatible textile of elongate shape comprising a medial end, a lateral end, a cranial part and a caudal part, the textile delimited by a peripheral outer edge formed of a convex medial edge, a convex cranial edge, a convex lateral edge and a caudal edge, and,
    at least one reinforcing element for the textile, the reinforcing element in the form of a resilient frame connected to the textile and set back from the peripheral outer edge, wherein the frame comprises a convex cranial segment extending from the medial end of the textile to the lateral end of the textile along the convex cranial edge, a caudal segment substantially extending from the medial end of the textile to the
    lateral end of the textile and caudally spaced with respect to the convex cranial segment, a lateral corner segment joining together the convex cranial segment and the caudal segment in the lateral end of the textile, a folding segment configured for joining a medial end of the convex cranial segment to a point located on the caudal segment while leaving a region of the medial end of the textile free of any frame, and a caudal extension located on the caudal segment and extending in a caudal direction toward the caudal edge of the textile.

2. The prosthesis of claim 1, wherein the frame is configured to adopt an unstressed configuration, in which the textile is deployed, and a stressed configuration, in which the frame is subjected to a transversal force directed towards the longitudinal axis and the convex cranial segment, the caudal segment and the folding segment are substantially collected together and aligned on one folding direction, the textile forming thereby at least one fold along the folding direction.

3. The prosthesis according to claim 2, wherein the lateral corner segment is linked to the convex cranial segment and to the caudal segment via two respective hinge points allowing the lateral region of the textile to be folded onto the remaining part of the textile.

4. The prosthesis according to claim 2, further comprising a deploying element located in a region of the medial end of the textile, for drawing away the convex cranial segment from the caudal segment when the transversal force is released and the textile is being deployed.

5. The prosthesis according to claim 4, wherein the deploying element is located inside a mouth defined by the folding segment and optionally the caudal segment.

6. The prosthesis according to claim 5, wherein the deploying element located inside the mouth is a tooth separate from the frame.

7. The prosthesis according to claim 5, wherein the deploying element located inside the mouth is an arrow separate from the frame.

8. The prosthesis according to claim 1, wherein the caudal extension includes undulations.

9. The prosthesis according to claim 1, wherein the caudal segment is concave.

10. The prosthesis according to claim 1, wherein the folding segment joins the medial end of the convex cranial segment to a medial end of the caudal segment.

11. The prosthesis according to claim 1, wherein the folding segment has a U shape extending towards a center of the textile.

12. The prosthesis according to claim 1, wherein the frame is continuous.

13. The prosthesis according to claim 1, wherein at least a part of the caudal segment has substantially the structure of a flat band forming undulations substantially in the plane of the textile.

14. The prosthesis according to claim 1, wherein the reinforcing element is molded over the textile.

15. The prosthesis according to claim 1, wherein the reinforcing element is made of bioresorbable material.

16. The prosthesis according to claim 1, in which the textile is a mesh.

17. The prosthesis according to claim 1, further comprising a grasping element capable of cooperating with a part of a grasping tool so as to temporarily couple the prosthesis to the tool.

18. The prosthesis according to claim 1, wherein the textile is bioresorbable.

19. The prosthesis according to claim 1, wherein the cranial part and the caudal part are asymmetrical.

20. The prosthesis according to claim 1, wherein the caudal edge is convex.

21. The prosthesis according to claim 1, wherein the caudal edge is flat.

22. A prosthesis for the repair of an inguinal hernia, of generally elongate shape defining a longitudinal axis aligned on a medial-lateral axis and a transversal axis aligned on a cranial-caudal axis comprising:

at least one flexible biocompatible textile of elongate shape comprising a medial end, a lateral end, a cranial part and a caudal part, the textile being delimited by a peripheral outer edge formed of a convex medial edge, a convex cranial edge, a convex lateral edge and a caudal edge, and, at least one reinforcing element for the textile, the reinforcing element being in the form of a resilient frame connected to the textile and set back from the peripheral outer edge, wherein the frame comprises a convex cranial segment extending from the medial end of the textile to the lateral end of the textile along the convex cranial edge, a caudal segment substantially extending from the medial end of the textile to the lateral end of the textile and caudally spaced with respect to the convex cranial segment, a lateral corner segment joining together the convex cranial segment and the caudal segment in the lateral end of the textile, a folding segment configured for joining the convex cranial segment to a first point located on the caudal segment while leaving a region of the medial end of the textile free of any frame, and a caudal extension located on a second point of the caudal segment and extending in a caudal direction toward the caudal edge of the textile, the first point being medially spaced to the second point of the caudal segment.

* * * * *